United States Patent [19]
Trudeau

[11] Patent Number: 5,980,447
[45] Date of Patent: *Nov. 9, 1999

[54] SYSTEM FOR IMPLEMENTING DEPENDENCY RECOVERY PROCESS

[75] Inventor: Guy J. Trudeau, Quebec City, Canada

[73] Assignee: Phase II R & D -Dependency & Codependency Recovery Program Inc., Quebec, Canada

[ * ] Notice: This patent issued on a continued prosecution application filed under 37 CFR 1.53(d), and is subject to the twenty year patent term provisions of 35 U.S.C. 154(a)(2).

[21] Appl. No.: 08/757,348

[22] Filed: Nov. 27, 1996

[51] Int. Cl.⁶ ....................................................... A61B 5/04
[52] U.S. Cl. ................................................................ 600/3
[58] Field of Search ........................... 600/300; 434/118, 434/236, 258, 307 R, 323, 350, 362, 365; 395/927; 345/302; 707/500; 463/42, 1; 607/45, 58, 900

[56] References Cited

U.S. PATENT DOCUMENTS

| | | |
|---|---|---|
| 4,639,222 | 1/1987 | Vishlizky . |
| 4,951,197 | 8/1990 | Mellinger . |
| 5,006,985 | 4/1991 | Ehret et al. . |
| 5,049,079 | 9/1991 | Furtado et al. . |
| 5,122,952 | 6/1992 | Minkus . |
| 5,207,580 | 5/1993 | Strecher . |
| 5,237,643 | 8/1993 | Kawabata et al. . |
| 5,320,538 | 6/1994 | Baum . |
| 5,344,324 | 9/1994 | O'Donnell et al. . |
| 5,377,258 | 12/1994 | Bro . |
| 5,387,164 | 2/1995 | Brown, Jr. . |
| 5,412,560 | 5/1995 | Dennision . |
| 5,435,324 | 7/1995 | Brill . |
| 5,435,725 | 7/1995 | Ikeuchi . |
| 5,503,561 | 4/1996 | Cohen . |
| 5,596,994 | 1/1997 | Bro ......................................... 128/904 |
| 5,678,571 | 10/1997 | Brown ..................................... 128/898 |

*Primary Examiner*—Samuel Gilbert
*Attorney, Agent, or Firm*—Jenkens & Gilchrist P.C.

[57] ABSTRACT

An interactive multi-media computer system for providing support and guidance to an individual undergoing recovery from a substance or emotional dependency. The computer system including a central processing unit, a monitor, user input device and a CD ROM for reading a pre-recorded medium containing interactive programming material. The CD ROM has data recorded on it for implementing computer routines which interactive engage the user and provide a crisis module for interactively testing and evaluating a user's mental condition and recommending specific procedures to come out of adverse mental conditions depending upon the results of the test. The CD ROM also contains a browse module with resource materials which are related to education in the realm of the recovery process and a quest module containing control software for structuring a specific program for the user to follow to further the user's progress in the recovery process.

10 Claims, 9 Drawing Sheets

| SPECIALIZED WWW SITES | PRODUCER MANAGER |
|---|---|
| DETAILED UNIVERSAL MEETING SCHEDULE: 120 FRATERNITIES 500,000 MEETINGS/WEEK/U.S. | FRATERNITIES/PHASE II |
| UNIVERSAL FRATERNITIES LITERATURE LIBRARY ALL BOOKS-PAMPHLETS CAN BE VIEWED AND DOWNLOADED AND ORDERED VIA BOOKSTORE | FRATERNITIES/PHASE II |
| SPECIALIZED LIBRARY | PHASE II |
| MEETINGS ON LINE | FRATERNITIES |
| CHAT LINE | FRATERNITIES |
| BOOK AND MEDIA REVIEW BEST-SELLERS, EDITOR'S CHOICE, REVIEWS | PHASE II |
| BOOKSTORE SPECIAL USER PRIVILAGES - BILLING SPECIAL DELIVERY IF DESIRED | PHASE II |
| SPECIAL INTEREST SECTION HAZELDEN-BETTY FORD-MAYO MEDITATION CENTERS - FOOD - LEISURE CHANNEL, ETC. | PHASE II |

*FIG. 8*

| OPERATIVE PRINCIPLES | TOOLS | EFFECTS |
| --- | --- | --- |
| 1. PAIN | BASIC PLATFORM | STARTER, TRIGGER MECHANISM |
| 2. H.O.W.[1] | PREREQUISITE | PROPER ATTITUDES |
| 3. DISCIPLINE | TRACER – PRIZE – DAILY USE | SELF ESTEEM/ RESULTS |
| 4. G.P.S. | TWELVE STEPS | SENSE OF DIRECTION: PAST/PRESENT/FUTURE |
| 5. KNOWLEDGE | TESTS-EVALUATIONS BOOKS WORKSHOPS OTHER | UNDERSTANDING FEASIBLILITY AND DEMONSTRATION: PROGRAM SOURCE, REPROGRAMMING AND DEPROGRAMMING |
| 6. FEELINGS | INTROSPECTION | DEALING, CHALLENGING AND REPLACING THEM |
| 7. SYSTEM | PROGRAM CONSTRUCTION | TIMELY PACING OF ACTIVITIES FOR MAXIMUM RESULTS |
| 8. MULTI-MEDIA INTERCONECTION | PC – CD-ROM PHONE – INTERNET TRACERS – TESTS | CONSTANT 24HRS/DAY VIGIL SUPPORT HUMAN PRESENCE AND GROUP |
| 9. INDIVIDUAL – TAILOR-MADE | SELF SPONSOR THERAPIST | PRECISE: FOCUS ENERGIES ON THE RIGHT TARGETS NO WASTE IN TIME OR EFFORT |
| 10. THERAPY | THERAPIST PLUS ALSO OTHERS AND GROUPS | SHORTCUT TO THE NEW WORLD WORK ON THE REAL ENEMIES SPOIL DEVIANT STRATEGIES BUILD – PROPEL GAME PLAN WITH ACTUAL POTENTIALITIES CONTEMPLATION OF FEASIBLE SUCCESS! |
| 11. GROUP SUPPORT | MEETINGS MEETINGS ON INTERNET FRATERNITIES | BREAK ISOLATION FEED COMPASSION AND COMPANIONSHIP POSITIVE ATTITUDES FEELING OF BELONGING |
| 12. H.O.W.[1] | REAFFIRMING SACRED VOW TO ONESELF FOR ONE DAY AT A TIME | EMPOWERMENT OF SELF |

[1] HONESTY – OPENNESS – WILLINGNESS

FIG. 9

SYSTEM FOR IMPLEMENTING DEPENDENCY RECOVERY PROCESS

BACKGROUND OF THE INVENTION

1. Field of the Invention

The invention relates to addiction recovery and, more particularly, to an interactive and computer based system for assisting individuals who are in the process of recovering from various addictive dependencies.

2. Description of the Related Art

Many people experience in their lives an addiction to various things which cause them to lose control over their lives and suffer periods of unhappiness. These addictions include chemical dependency, e.g., an addition to alcohol, drugs, or food; behavioral dependency, e.g., an addiction to gambling or sex; and co-dependency, an addiction to the behavior of other people. The process of coming out of these addictions includes at least two steps: rehabilitation and recovery. Rehabilitation is the process by which an "addict" learns to abstain from addictive substances or behavior while recovery is the inner healing process by which a former addict returns to full and complete mental health.

In the early part of this century there were virtually no treatments for addictive behavior. Addicts were censored by society and either thrown out on the street, jailed or hospitalized. A major revolution in the treatment of addictive behavior occurred in 1935 with the advent of Alcoholics Anonymous (AA) which promulgated a twelve step program by which an addict could escape the clutches of his or her addiction and reassume control over his/her life and relationships. A fundamental part of the AA program is that alcoholics must stop denying their addictions and take responsibility for their actions. Such responsibility includes the attendance of regular meetings of recovering alcoholics which provide both perspective and group support to an individual undergoing the addiction recovery process. In 1955, the American Medical Association (AMA) defined alcoholism as a disease and removed a certain amount of stigma associated with it and thereby furthered the process by which people could come out of their addictions. Since 1935 the AA program, the twelve steps, the so-called Big Book and other literature along with thousands of support group meetings available each day across the United States and the world have changed the lives of millions of people.

The AA program has been emulated by many other fraternal organizations and today there are some 120 fraternities in the United States devoted to assisting its members in their recovery from addictions. These organizations sponsor over 500,000 meetings in the United States each week and are attended by upwards of 10 million individuals. However, despite the enormous progress of addiction recovery techniques on both social and individual levels, the distress of those in the recovery process remains high.

It is generally taken to be true that among the total population of dependents and co-dependents, 33% will never obtain complete abstinence from the object of their addiction; 52% will abstain from the object of their addiction but will carry on their lives with various degrees of so-called "dry drunk" behaviors and attitudes; and only 15% will fully recover. Addiction is a response: a response to pain. These statistics mean that a huge number of people will remain in deep pain throughout their lives unless they can successfully accomplish full recovery and return to complete mental and physical health.

Over the years since the advent of the AA program in 1935, many changes have taken place in the therapeutic mechanism used in the treatment of addictions. Among these, there have been significant changes in psychological treatment techniques, in communications and in data transfer and availability. Addiction is now perceived to be a family disease in which both the individual dependent and his or her spouse have problems to face. Other changes in therapeutic addiction recovery techniques are grounded in the understanding that traits, profile and behaviors of a "significant other" toward the addict frequently fall within the description of the term "co-dependent." Moreover, addictions and other forms of dysfunctional behavior have been shown to be passed on from generation to generation. The pain associated with this behavior is usually rooted in the "child" within each individual implying that dysfunctional behaviors and strategies are generated as a response to conditioning formed during very early years of development, i.e., 0–6 years old.

Throughout this period, however, various self help groups, meetings and sponsors implemented by AA, the twelve steps and the Big Book, have accomplished enormous results for literally millions of people.

On the downside of dependency recovery developments during the past 60 years, classic psychiatry has been of little help with respect to the large populations of persons who are both still in the throes of addiction and those attempting a recovery process. Around 1955, Professor Albert Ellis began the postulation and structuring of Rational Emotive Therapy (R.E.T.) with the publication of numerous books which expounded its principles in conjunction with Behavioral Therapy (B.T.). In addition, significant progress has also been made through Cognitive Therapy and the contributions of Dr. Aaron Beck who has supplied many potent tools useful in the recovery process. AA has chosen to remain linear in its program and teachings and has not integrated other findings and therapies into its program. In addition, academia, classic psychology and psychiatry have very little to do with therapy groups, meetings, the twelve step process or its spirituality components regardless of whether it is of the faithless or faithful format. Moreover, classic psychology and psychiatry have restricted themselves to "1-on-1" therapy in an office setting rather than attempting any integration with other successful tools for addiction recovery.

The history of addiction recovery over the last 50 years indicates the need for better programs and tools for assisting those undergoing the recovery process. The American Psychiatric Association estimates that approximately 8% of the adult population in the United States is dependent upon alcohol. The same percentage is considered to be at risk of abusing alcohol. Today alcohol and chemical dependence is considered to be a family disease directly correlated to the existence of co-dependence in personal relationships thereby affecting both the children and the spouse of the addict. For example, teen-age children may, due to peer pressure and/or a lack of self-esteem, engage in habitual behavior which is both addictive and destructive in nature. Notwithstanding other chemical dependencies and other types of behavioral dependencies, i.e., just looking at the statistically extrapolated numbers related to the abuse of alcohol together with its effect on the spouses of addicts, something on the order of 30% of the entire adult population of the United States may be involved. If, for the sake of argument, other known dependencies such as food, drugs, sex, work, gambling and the like are included, the number of persons affected by addictions in the United States may be on the order of 50% of the adult population.

Many persons who are dependent rely upon the professional care of a rehabilitation center to assist them in working their way out of their dependence, while many try to extract themselves alone. Regardless of which path they follow, most recovering addicts are susceptible to slips and relapses. Invariably, all experience the "black hole" of recovery, and, instead of getting better, they may get worse. While undergoing recovery, numerous feelings and emotions start to command the recovering addict's attention and self evaluating questions proliferate, such as: Why did I do that?; Who am I?; What prompted my behavior in the first place?; How do I deal with all this pain?; Can I really recover?; What are the paths to recovery?; Will it work?; How much effort will it take?; Can my behaviors really be changed?; and many others. All persons undergoing recovery relive the trauma from the past and the questions and the nightmares of waking up and not knowing where to go or how to get there.

For certain reasons, there is very little social support for persons recovering from addictions. Support comes almost exclusively from the numerous fraternities which have developed, such as Alcoholics Anonymous (AA), Overeaters Anonymous (O.A.), Cocaine Anonymous (C.A.), Gamblers Anonymous (G.A.), Adult Children of Alcoholics (ACOA), Co-Dependants Anonymous (CODA), AL-ANON (for the spouses of alcoholics), ALA-TEEN (for the teenage children of alcoholics) and others. AA has single-handedly assisted in the recovery of millions of people and spawned a following with such momentum that today there are approximately 500,000 groups that meet each week in America. This includes upwards of 10 million individuals attending meetings each week.

Most of the addiction recovery support fraternities take for granted that full recovery takes more than five years; the first five years "being the worst." It is unquestionable that recovery is a very slow and painful process and one can do little more than go to support group meetings, follow the guidelines from the twelve step process, and read a few books.

Significant changes come to the recovering addict through a number of different sources. For example, within the realm of psychology and psychiatry, the tools and methods recently developed are both efficient and effective. From rehabilitation centers, notably those associated with the Hazelden Foundation, and from leading practicing therapists we have recently witnessed the emergence of rich structural concepts such as generational dysfunctionality and co-dependence which are extremely helpful in the recovery process. In addition, useful books and numerous tools for testing, monitoring, evaluating and scoring those engaged in the recovery process are very helpful.

For those interested in the recovery process, the debates regarding the value of different therapeutic techniques range between science and community concerning the acceptability of new concepts and the usefulness of spirituality in the recovery process. Although the majority of dependents and co-dependents find many of the new concepts useful and also believe that some spirituality is important in the recovery process, nevertheless the debate continues. For people actively involved with assisting recovering addicts, the only relevant issue is efficiency. When a practice gives good results in recovery and when concepts are helpful in finding a way out for the person who is suffering, they are deemed to be useful and rewarding.

Spirituality has been shown to be a key element in assisting individuals in the recovery process. This involves two forms of spirituality: faithless and faithful. Faithless spirituality results from the general positioning system needed by an addict in the first and second phases of rehabilitation and recovery. It corresponds to a buildup of some essential metaphysical questions concerning self, others, the world and the general acquisition of relationship and forms of power. Faithless spirituality relates to destiny, to freedom, to powers of the universe and not to notions of a higher power. On the other hand, the "faithful" form of spirituality is that by which the individual integrates some attributes of reciprocity into these relationships and perhaps elements of finality. Spirituality, whether of the faithless or faithful type, is something misunderstood when it is deemed to belittle individuals. For most people, the very great majority of dependents and co-dependents, the integration of this dimension of faith assists in finding, articulating and incorporating the principles and guidelines into one's own self and consequently into action.

While many individual elements have proven to be useful in the recovery process, there remains a great need for coordinated and well defined integration of the various elements of a successful recovery into a single system. The system of the present invention proposes a new tool and methodology for programming recovery from various addictions.

BRIEF SUMMARY OF THE INVENTION

One object of the present invention is to rank in frequency and duration of use, as well as timing and scheduling, the mastering of recovery tools as well as the tracking and recording of a subject's progress in recovery. Another object of the invention is to reduce the level of pain experienced by a recovering addict during the process of recovery.

A still further object of the present invention is to establish obtainable goals of recovery well within a period of approximately two years and during that process, provide both quantitatively and qualitatively measurable progress.

The system of the present invention generates a change environment for addiction recovery. It includes a self-administered individual interactive recovery program for dependents and co-dependents. Interaction between the user and the process incorporated into the present invention shapes and defines the program itself via user defined profiles through test results and the incorporation of options and selections into the system. The system of the present invention both directs the user out of crisis as well as proposes a blueprint for the recovery process itself by providing activities for: (a) defining dysfunctional behaviors and defeating strategies; (b) mechanisms for bypassing denial; (c) accessing and accepting feelings and identifying their true cause; and (d) providing new strategies and mechanisms for neutralizing dysfunctional behaviors by developing new programs, attitudes and behaviors and for the development of new skills. In addition, the present invention provides massive amounts of specific, targeted, and productive information which is custom configured for the individual recovering addict's profile. It also provides specific achievement modules and a mechanism by which programs and systems are adapted to the evolving profile of a specific user.

In one aspect the present invention includes an interactive multi-media system for providing support and guidance to an individual undergoing recovery from a substance or emotional dependency. The system includes a computer system having a central processing unit, a monitor, user input means and a recorded media reader for reading a pre-recorded medium containing interactive programming material. The recorded medium has data recorded thereon and is adapted for interactive engagement with the user of the computer system so that the recorded data controls said computer system to implement a plurality of operational modes. These modes include a crisis mode for interactively testing and evaluating a user's mental condition and recommending specific procedures to come out of adverse mental conditions depending upon the results of the test; a browse mode containing resource materials for the user of the computer system related to education in the realm of the recovery process; and a quest mode containing means for structuring a specific program for the user to follow to further the user's progress in the recovery process.

In another aspect the present invention includes a method of providing interactive support and training to an individual undergoing a process of recovery from substance/emotional dependency. The method is performed within a computer system programmed for interactive engagement with the individual and provides the individual with a selectable choice from plurality of interactive modules each module comprising information stored on a prerecorded medium in the computer. At least one of the choices includes a computer controlled routine for interactively testing the individual user to evaluate the level of distress the individual is experiencing at the present moment, evaluating the result of the test to produce an output and, based upon the test output, providing to the individual a strategy of action to alleviate the distress.

In a still further aspect the present invention includes a data carrying medium having data recorded thereon for controlling an interactive computer system. The recorded data is organized into a plurality of software modules which modules include a crisis module containing a plurality of user selectable standardized tests, each of which are capable of indicating the distress level of an individual taking the test. Other software modules define means for interactively receiving test response information from the user and, based upon those responses, evaluating the distress level of the individual completing the test as well as means responsive to the distress level indicated by the results from the selected test for recommending to the user a specific action to be taken in order to moderate the level of distress indicated by the results.

In yet still another aspect the present invention incudes a computer program product having computer readable medium having computer program logic recorded thereon for controlling a computer to establish an interactive system for providing support and education to a user undergoing a process of recovery from substance or behavorial addiction. The computer program product incorporates at least one distress evaluation test into a menu of choices for the user. The responses to there choices indicate a level of emotional distress being experienced by the user at that time. The computer program product presents the choices to the user to administer the test and is then responsive to the user's choices in the evaluation of the user's current distress level. Additionally, the computer program product responds to the current distress level of the user indicated by the test evaluation by proposing to the user a strategy of action to appropriately deal with the indicated current distress level.

BRIEF DESCRIPTION OF THE DRAWINGS

A more complete understanding of the method and system of the present invention may be obtained by reference to the following detailed description of the preferred embodiments that follow, taken in conjunction with accompanying drawings, in which:

FIG. 8 is a table illustrating certain aspects of an exemplary software browse module incorporated into the system of the present invention;

FIG. 9 is a table illustrating certain parameters associated with the operative principles incorporated into the system of the present invention.

DETAILED DESCRIPTION OF THE PREFERRED EMBODIMENT

As discussed above, there are numerous tools useful to one degree or another to an individual undergoing the process of recovery from an addiction. It has been found that some of these tools are more helpful than others and also that the use of these tools in specific combinations and specific inter-relationships provide greatly enhanced results with respect of the rate of recovery. The system of the present invention incorporates multiple tools in custom configured combinations and has been found to drastically accelerate the recovery process. A recovery that usually takes between five and eight years may be accomplished in approximately two years. More particularly, the system of the present invention integrates a computer-based multi-media delivery network with other conventionally available tools to virtually custom configure the recovery program for each individual.

Figure 1:
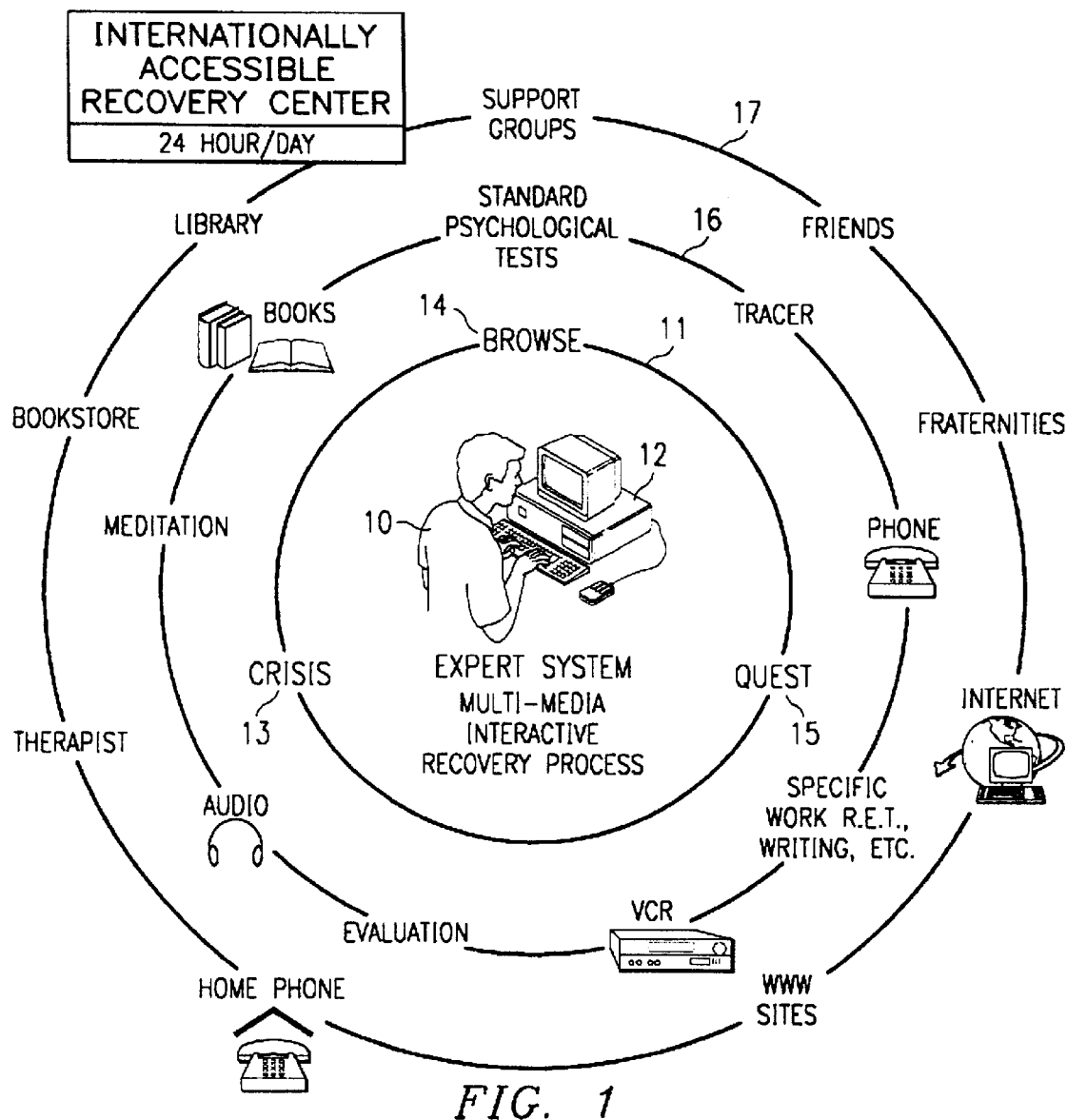
FIG. 1 is a pictorial diagram illustrating various aspects of the recovery tools available and associated with the present invention.

Referring first to FIG. 1, there is shown a pictorial diagram illustrating an individual 10 in engagement with the multi-media system forming one aspect of the present invention 12 and selectively passing through its three modes of functionality: a crisis mode 13, a browse mode 14 and a quest mode 15. The system of the present invention is incorporated into the recovery center core 11 and enables the individual 10 to also selectively interact with an intermediate level of recovery tools 16 and an outer level of recovery tools 17. The present system enables the individual 10 to selectively draw upon the tools in these different levels in a manner which is custom configured for the state of mind of the individual at the time it is being used as well as the level of progress the individual has reached at each point in his or her recovery process.

Figure 2:
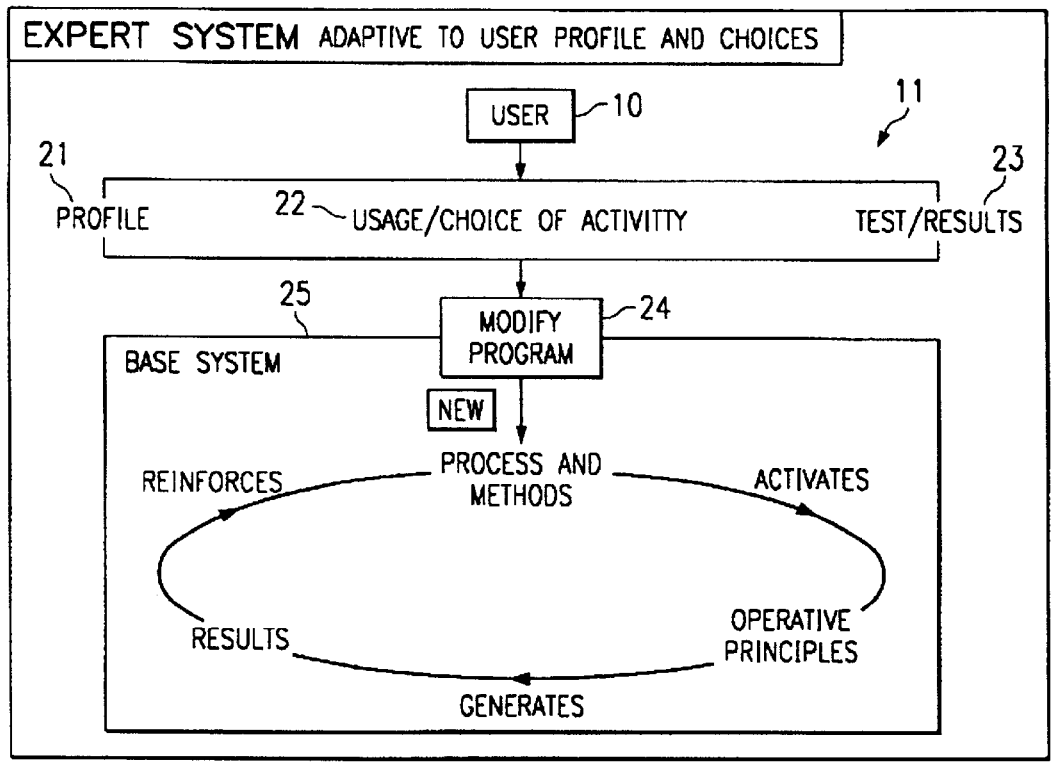
FIG. 2 is a block diagram illustrating one aspect of a user's interaction with the system of the present invention.

Referring next to FIG. 2, the multi-media interactive recovery system of the present invention 11 is illustratively shown with the user 10 interactively engaged with a plurality of different modes of operation. These include those which extract and/or prepare a profile 21 of the user's mind state and level of progress at the time: those which select a mode of usage or choice of activity 22 for the user; and those which administer evaluative tests and produce results 23. Based upon these interactions by the user 10, the system modifies the program to be followed by the user by introducing new processes and methods into the program thereby activating certain operative principles which by their very nature generate certain results for the user and thereby reinforce the incorporation of the new processes and methods under use. All of which takes place within a base interactive system 25.

Figure 3:
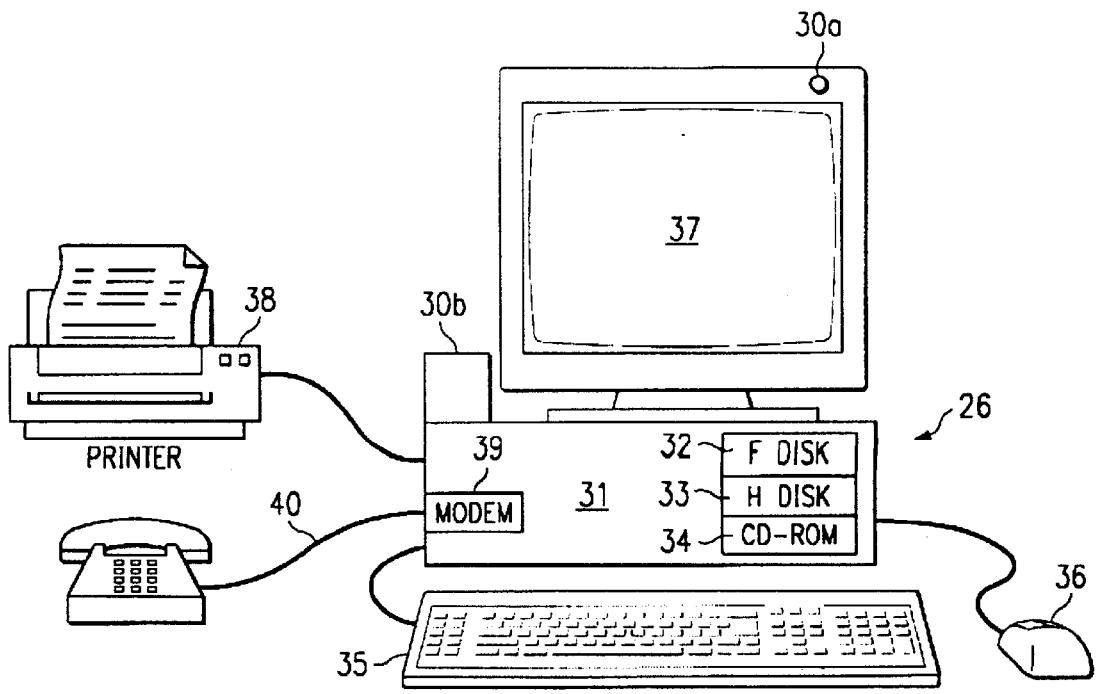
FIG. 3 is a block diagram showing an interactive multi-media computer system used in the implementation of the present invention.

Referring next to FIG. 3, there is shown a personal computer (PC) system of the type which may be used in the implementation of the system of the present invention. The computer system 26 includes a central processing unit 31 containing one or more microprocessors and, for example, a floppy disk 32 for the input and output of information from the system, a hard disk 33 for the storage of programs and information on the system and a CD ROM drive 34 for the reading of interactive media recorded on a CD ROM and used in the implementation of the system of the present invention. The computer system 26 also includes a keyboard 35, a mouse 36, and a microphone 30*a* for user input and a monitor 37 and speaker 30*b* for user output. A printer 38 is included along with a modem 39 used for accessing the telephone network 40 for several different purposes, including database and data communications network access such as the Internet, as described below.

Figure 4:
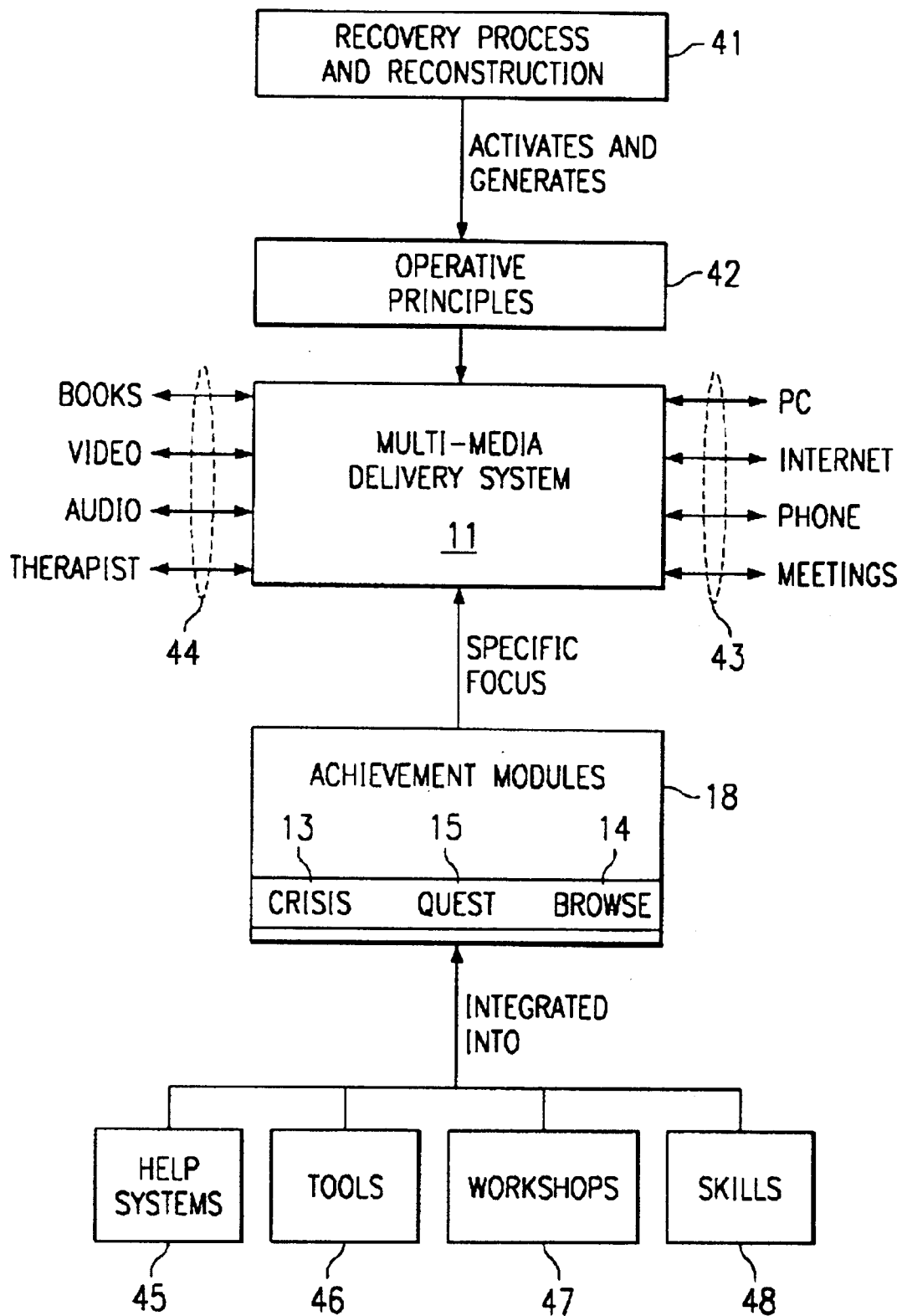
FIG. 4 is a flow chart illustrating an overview of the operative elements involved in certain aspects of the system of the present invention.

Referring next to FIG. 4, there is shown a flow chart depicting the interaction of the various conceptual elements incorporated into the system of the present invention. First, entry into the recovery process in order to reconstruct the life of the individual undergoing the recovery process is represented as the starting point at 41. Volitionally entering into the recovery process activates and generates certain operative principles at 42 which will be explained in more detail below. These operative principles are implemented by means of the multi-media delivery system 11 forming part of the system of the present invention. The central core delivery system 11 incorporates the PC system 26, discussed above, as well as other resources and tools depicted in both grouping 43 and 44. The multi-media delivery system 11 also enables the user to interact with a plurality of achievement modules 18 comprising the crisis module 13, the quest module 15 and the browse module 14. Integrated into each of these modules are help systems 45, various recovery tools 46, workshops 47 and skills training 48. The multi-media delivery system 11 effectively achieves superior results by a combination of basic operative principles, knowledge, matrices, tools, support services, workshops, progressively structured learning modules, various skills and interaction with technology.

Figure 5:
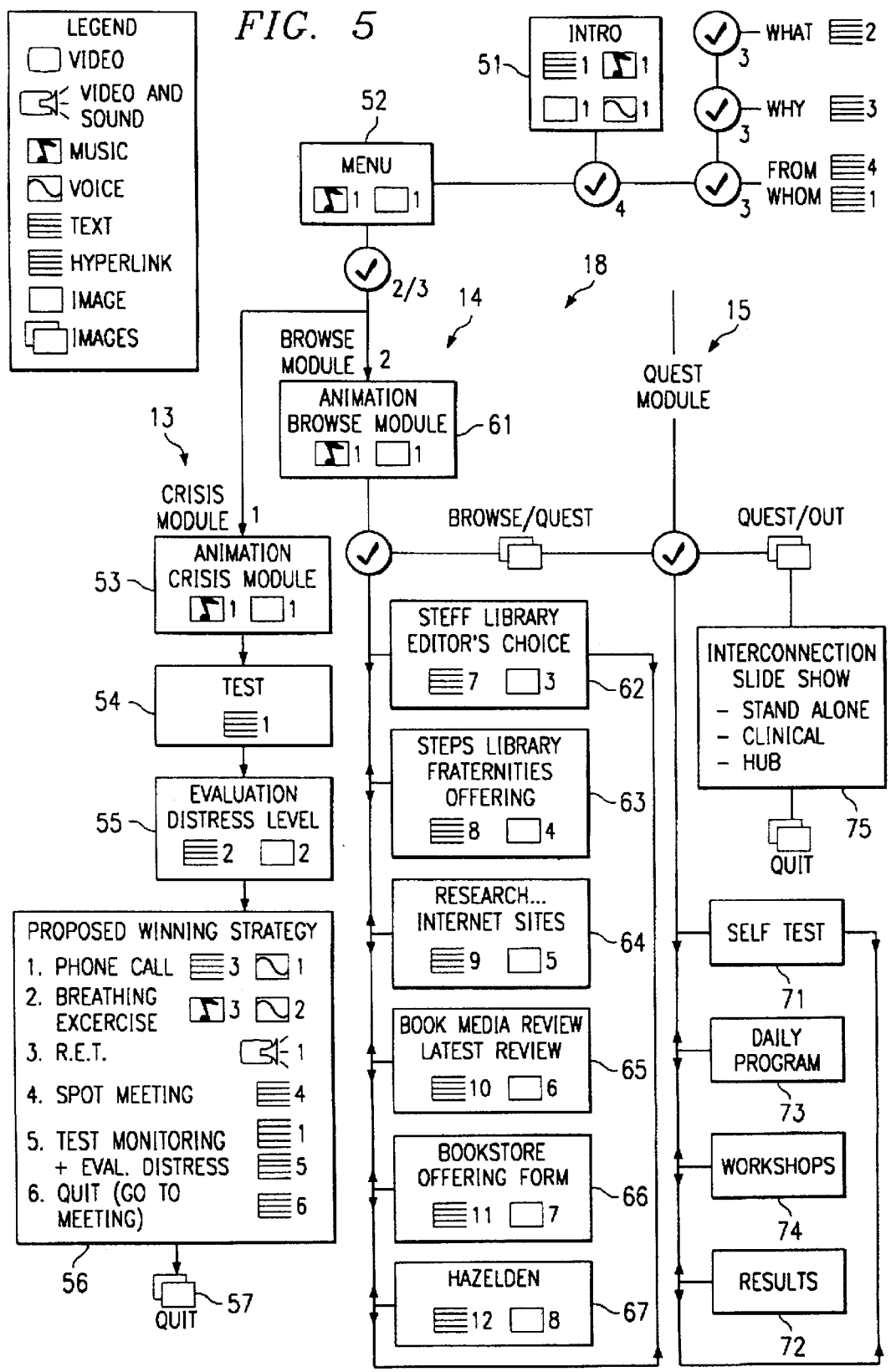
FIG. 5 is a flow chart illustrating certain aspects of the software and methodology used in the system of the present invention.

Referring to FIG. 5, there is depicted an overall architecture of the multi-media interactive recovery system of one aspect of the present invention. In general, the diagrams of FIG. 5 pictorially illustrate the choices available to a user engaged in interaction with the system.

Following an introduction 50, which may include graphics, sound and animation, the user enters an individual registration profile module which is used to collect information about the individual user and to assemble a database within the system which represents the individual user's personality/recovery profile. This initial data gathering aspect of the invention is a very important component and will be used in the other modules of the system, particularly the crisis module 13 to guide the inference engine of the expert system in its decision making processes. Upon entry into the registration profile module 50, the initial interactive engagement between the user who is registering and the system is executed in a three part process referred to as the "specific individual registration profile imprint." This process includes: (a) an interactive questionnaire soliciting information from the user; (b) one or more tests administered to the user; and (c) and the solicitation of information and generation of a "storyboard" representing the registering user's past personal/psychological history and personality characteristics.

The interactive questionnaire for gathering facts about the registering user is implemented by means of a series of data soliciting questions pertaining to a wide variety of topics. These topics may include: age; sex; address; academic history and background, physical and mental health; prior association and history with fraternal recovery organizations including name of the user's current sponsor; various telephone numbers such as therapist, friends and sponsor; social number ID; choice of billing vehicle with respect to additional service charges, credit card numbers, calling card numbers and other related data. All of this information is stored within an encrypted cache on, for example, the hard disk 33 of the computer system 26 shown in FIG. 3.

The second part of the individual registration profile process i.e., the profile test to be administered to the registering user, is the administration of one or more tests, the results of which establish a baseline with respect to the personality profile of the user. These tests are chosen from many currently available and widely accepted tests and include: (a) a test indicating psychological profile dominance; (b) a test indicative of the user's tendency toward moods and mood intensities; (c) a test reflective of the user's life themes; (d) tests related to the user's overall distress levels for each area of life theme or sphere of life; and (e) tests indicative of the user's recovery objectives per sphere of life. The results of these tests are referred to hereinafter as "Passport #1" and form a baseline of personality profile data also stored as encrypted information within the system, for example, on hard disk 33 of the computer system 26.

The final component of the three part individual registration profile process is the preparation of storyboard, referred herein as "Storyboard #1." In general, Storyboard #1 is constructed as a work in process comprising a storyboard or storybook chronicling a registered user's life. It is an initial structuring of an ongoing process of the reconstitution of the user's self in terms of incidents, accidents, faults, failings, turning points and other significant milestones and events in one's life. Storyboard #1 includes both facts and figures taken from the questionnaire as well as profiles, measurements and objectives taken from the testing phase to form Passport #1. The storyboard is continuously worked on and modified as part of the recovery process facilitated by the system of the present invention. It is used in both the crisis module 13 and the quest module 15 to objectively view incidents in the user's life together with reactions and behaviors which have been acquired over user's life together with personality deficiencies and examples of dysfunctional behavior in order to formulate strategies and cognitive functional responses.

Each of the above three elements of the individual user registration process i.e., facts, profiles and storyboard and periodically modified and are evolutionary in nature. However, the system operates to maintain specific versions of each of these elements in a ciphered cache within its memory to provide a database comprising a baseline against which the user can view his progress.

As can be seen below, the initial entry module 50 of the system and the formulation of a baseline of information with respect to the registered user who will be using the system is important. Numerous decisions and recommendations are made by the system based upon this information.

Following initial assembly of the user's personality/recovery database at 50, the user enters a menu 52 from which can be selected, either the crisis module 13, the browse module 14 or the quest module 15. Each of these modules may be selected depending upon the mind state and purpose of the user at the particular time he/she accesses the system. For example, if the user is having a very bad day and is effectively having a mental crisis over a desire to return to old habits (for example, to again use alcohol or drugs) or his/her perceived lack of progress in the recovery process, or even suicidal inclinations the crisis module 13 might be accessed. In a first sub-module comprising a set of routines 53 the user is introduced to the crisis mode via animation and other communications tools and induced to take a test at 54 to try and ascertain the level of distress that the user is experiencing at that moment. At 55 the results of the test are delivered and at 56 a strategy is proposed for dealing with the crisis depending upon the nature and level of distress indicated by the evaluation. The proposed strategy is selected from a plurality of alternative choices depending upon the results of the test and, in some cases, the profile of the user. For example, in cases of severe distress levels, e.g., suicidal tendencies, a phone call may be automatically placed by the system to a crisis intervention counselor through a telephone access such as a 1-900 number. Alternatively, the system could suggest that the user engage in a prescribed series of breathing exercises to attempt to recover some of the balance of the user's mind in the presence of a crisis before taking further action. Another alternative which could be directed by the system is Rational Emotive Therapy (R.E.T.) or the entering into an on-line fraternal meeting via Internet access. Further tests, monitoring and evaluation of the distress level can be administered in the context of proposing a strategy of action or it may be suggested that the user simply quit the program at 57 and go immediately to attend one of the fraternal meetings in the local area, a list of which is carried within the program or accessed via the Internet.

As mentioned above, one action to be taken by the system would be the dialing up and connection of the user to a trained therapist via a 1-900 number. In which case, the system contemplates the downloading of information from its database to a module associated with the user terminal of the trained therapist. For example, as the call is placed, it would employ protocols, such as file transfer protocol (FTP) to download selected information from the baseline data, for example the user's profile, characteristics and storyboard to a central location where the therapist is located. Such transfers of data both from the PC to a remote location as well from a remote location to the PC of the user can be accomplished with one of many readily available data transfer protocols and enables the sharing of information as a part of implementing the system of the present invention. In addition, a user can initially register with a 1-900 counseling service and in so doing download an encrypted version of his baseline psychological profile information into the database of the service. Thus, upon delivery of a password by telephone, even if the user was not currently using the computer system of the present invention, a therapist could access the user's database for assistance in rendering counseling services to the user.

Should the user at 52 elect the browse module 14, following introduction of the module itself through animation, graphics and sound at 61, the user may selectively access one of multiple information resources made available through the system. For example, at 62 there is shown sub-module containing a library of books and other audio-visual materials especially selected for inclusion within this system while at 63 there is a library of offerings from the various recovery support fraternities such as AA. At 64 a plurality of hypertext links to various research sites on the Internet would be provided and at 65 a review of the latest books and other media is given. At 66 a hypertext link to an on-line bookstore is provided and at 67 hypertext links to various sites of major addiction treatment centers such as the Hazelten Foundation, the Betty Ford Foundation etc. are provided. These choices enable the individual undergoing recovery to have at his or her fingertips a plurality of resources helpful to them in the recovery process.

If, at 52, the user selects the quest module 15, there is provided access to a plurality of sub-modules for use by the individual in transition through the recovery process. For example, at sub-module 71 there is provided a plurality of self tests in which the user can periodically test for mental attitude and/or progress in the recovery process and receive the results at sub-module 72. At 73 there is provided a sub-module through which the user can structure a daily program of both activities and interactions with the system of the present invention which are educationally helpful and emotionally supportive in the recovery process. An illustrative program will be given in more detail below. Finally, at 74 there is provided access to a plurality of workshops either directly carried by the recorded interactive media in use or on other media such as separate video tapes and audio recordings.

The system also provides for interconnection to other helpful routines at 75 whereby the user can access certain other resources with respect to use of the system.

The life of a rehabilitated dependent and that a recovering co-dependent is usually, at least for the first few years, a challenging series of cyclic ups and downs of various intensity. These cycles often lead to slips and relapses slowing the recovering process. They also contribute to making life miserable for the individual. Therefore, the system provides tools to warn against relapse, tools to measure the state of mind and feeling of the individual as well as tools to guide and direct one out of a crisis.

In many ways, the crisis module is one of the most important modules in the system of the present invention. For this reason, the emphasis in the system upon entry into the crisis module is testing in accordance with certain of the most commonly used and widely accepted distress evaluation tests. Thereafter, the test score is introduced into a psychological matrix, compiles recommendation from the user's profiles and other baseline data and can incorporate an inference engine driven expert system to recommend certain remedial actions in response to these parameters. These actions include, in the case of severe distress, a screen indicating immediate danger to one's self and others; direction of the user to tools most capable of lowering distress; and other recommendations depending upon the nature and the acuteness of the crisis. The crisis module ranks the available tools in a simple progression of stress reducing actions. The two principle goals to be achieved by the crisis module are to intervene in the crisis and lower distress to enable the individual to get back to managed emotions and, if possible, give a sense of security and provide hope for recovery.

Figure 6:
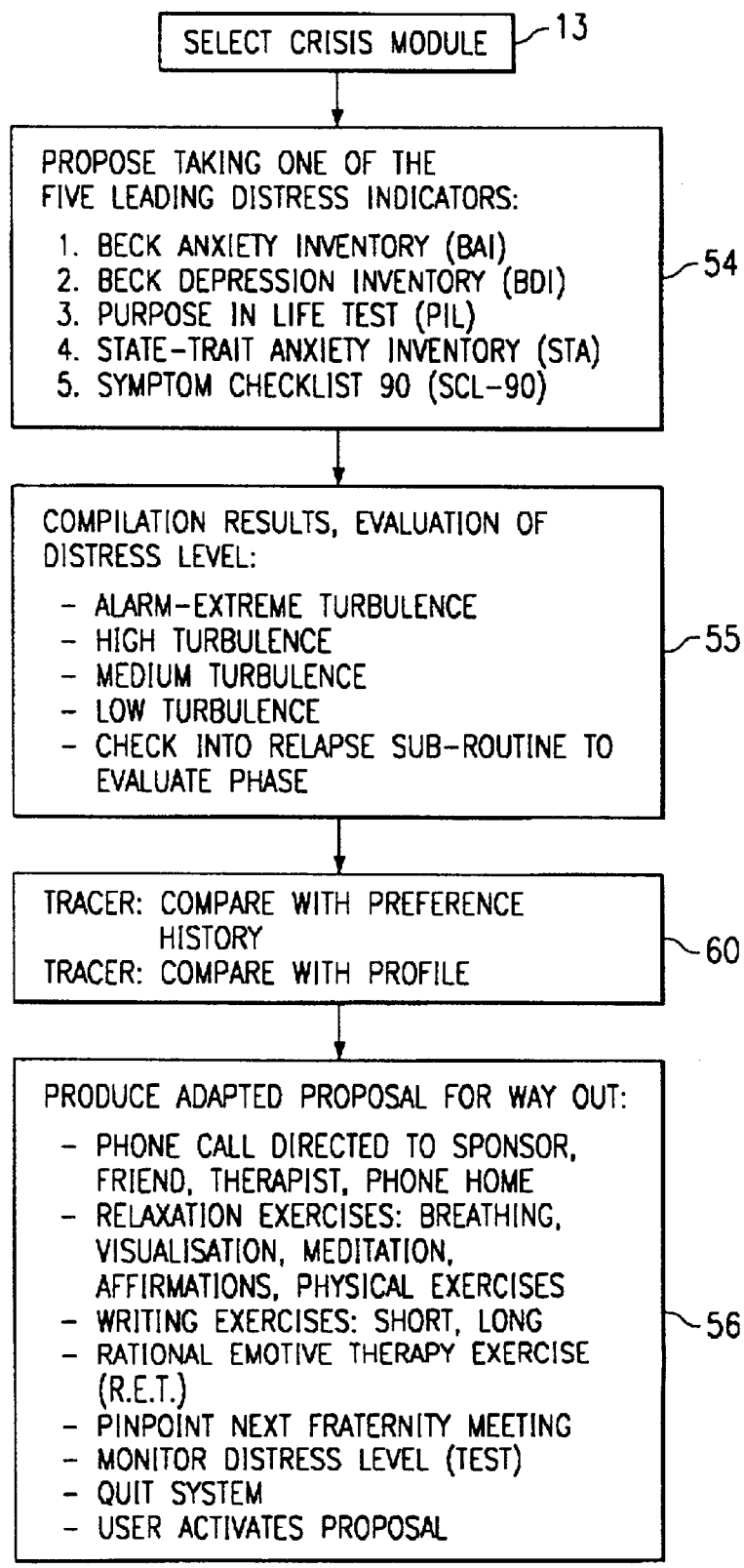
FIG. 6 is a flow chart depicting various aspects of an exemplary crisis software module employed in the system of the present invention.

Referring next to FIG. 6, there is shown a flow chart indicating in more detail the functional interactivity associated with the crisis module incorporated into the interactive multi-media delivery system of the present invention. As described briefly above, a user selecting the crisis module is provided with access to one of a plurality of standardized tests capable of indicating stress level within an individual. In sub-module 54, for example, the user is offered a choice between 5 distress indicating tests: Beck and Anxiety Inventory (BAI); Beck Depression Inventory (BDI); Purpose-In-Life (PIL); State-Trait Anxiety Inventory (STA); and Symptom Check List 90 (SCL-90). It should also be understood that this list might be modified depending upon an initial profile of the individual user input into the system when usage is first begun. Once a test is selected and completed in a very straight forward manner by interactively answering queries displayed on the monitor, the system evaluates the answers of the individual and at sub-module 55 compiles the results of the selected test and gives an evaluation of the distress level currently being experienced by the individual based upon the test results. These might include, for example: alarm-extreme turbulence; high turbulence; medium turbulence; low turbulence; and an opportunity to exit into a relapse sub-routine to evaluate a particular phase. Once a test evaluation is provided within the system, at sub-module 60, a comparison of the test results may be made with the history of the individual as well as with the profile of the individual initially input into the system through a separate set of queries described below.

A principal basis upon which the system of the present invention analyses the results of the test (a) administered in submodule 54, is the processing of the results of those tests in light of the individual registration profile imprint of the user gathered in module 50. The algorithms of the inference engine of an expert system in the present invention derives its inferences from a number of different parameters. The first of these includes a psychological profile assembled on the user from the individual registration profile imprint including a characterization of the user as having a particular profile, for example: workaholic; people pleaser; caretaker; martyr; perfectionist; tap dancer, etc. In addition, the system also considers the test results information from the standpoint of a "drama triangle" analysis including the preclassification of the individual user as either victim, persecutor, or savior. Another parameter considered relates to the psychological characteristics of the user including the user's deficiencies and the dysfunctional strategies associated with the individual psychological profile of the user and that user's position within the drama triangle.

The inference engine performs to establish a cognitive profile of the individual including the following elements: the user's sense of self; the user's sense of others; the user's sense of life and future prospects; and the user's dysfunctional strategies, dysfunctional consequences, and behaviors. Each of the elements defining the user's cognitive profile are significant elements used in the diagnosis of the mood/distress level of the individual indicated by the distress indicating test compiled at submodule 55. Moreover, the user's perceived change via the test in moods and quality of life is also considered. The information from each of the sources of input to the inference engine is dealt with by means of algorithms to produce a diagnosis of the current mental status and distress level of the individual to produce a conclusion indicating suggested tools and/or activities for the user to remedy the current level of distress.

The inference engine algorithms are preferably based upon decisions structured in a "if . . . /then" format. Essentially the test results produce a profile that generates a series of behavioral characteristics. These characteristics produce behaviors that can be tackled via priorities that are inferred as the counterpoints/strategies comprising the opposers of the current mood.

Moreover, in the present system, the individual user profiled infers certain deficiencies inherent in compensatory behavior as well as certain tendencies toward moods and levels of distress. The test administered infers currently experienced moods and levels of distress as well as quality of life as perceived by the individual having taken the test. The mood and level of distress also infers certain activity programs while the profile dominance or prioritization change with either the test or by the volition of the individual. Prioritization includes: profile, characteristics, deficiencies, and compensatory behavior all which change the inference engine structure to respond to the situation by means of the "if . . . /then" decision tree.

In response to both the compilation results of the test at 55 and a comparison with base line information at sub-module 60 the system produces an adapted proposal to the individual proposing a strategy for coming out of the current distress. For example, in the most severe alarm level turbulence, the system could automatically place a phone call directed to the individual's sponsor (one who has taken personal responsibility for the individual's recovery process in accordance with principles of current recovery fraternities such as AA), a friend, a therapist or a 1-900 call to a system manned by trained therapists. Each of these phone calls would be automatically placed by the system in a pre-selected priority based on preprogrammed phone numbers and information. Secondarily, in somewhat less distressful circumstances, the system might suggest relaxation exercises, breathing exercises, visualization, meditations, affirmations, physical exercises and other tools which are useful to lower the level of stress in an individual currently experiencing a crisis mode. Further, certain writing exercises might be directed in order to again distract and lower the stress level of the individual or Rational Emotive Therapy exercises could be prescribed by the system to deal with the stress currently being experienced. Additionally, the system could pinpoint the next fraternity meeting based upon both internally stored information as well as information readily accessible via the Internet. Finally, the system may suggest an additional test to determine if any of the aforementioned stress reducing activities had produced an effect upon the distress level of the individual. The individual would, in conclusion, quit the system and activate the proposed proceedings suggested by the system.

The browse module is principally about community and belonging, each of which assist in breaching the isolation of the individual undergoing recovery. The browse module feeds information to the individual about realities and activates group dynamics, identification and sharing. It provides a wealth of information available to the person to assist them in the recovery process.

As pointed out above, when the user accesses the browse module 14, there are available a number of possible databases and other sources of detailed information that can be provided to the user both as part of a library of information stored on the media, such as a CD ROM implementing the system within the PC, but also via hypertext links to specialized worldwide web Internet sites preprogrammed into the media thereby enabling quick access by the individual. Depicted in FIG. 8 is a plurality of such specialized worldwide web sites and an indication as to what type of organization would be the producer/manager of such sites. Illustrated are the detailed universal meeting schedules of some 120 various addiction recovery support fraternities in the United States (comprising 9 basic organizations and over 100 subsidiaries thereof) having on the order of 500,000 meetings per week within the United States. This information is compiled and maintained by the fraternities themselves as well as the organization providing the recorded media used to implement the present invention. In addition, there are a large number of generalized libraries as well as specialized libraries providing additional information to one seeking such information. Support meetings are available on-line via the Internet at which individuals can participate in a fraternal style meeting from their own PC. The system also implements "chat" lines to talk to one or more persons via the Internet who may be able to provide support and assistance to the individual. Book and media reviews are also contained on the media as well as hypertext links to one or more on-line bookstores for obtaining additional publications and other information by mail. Finally, special interest sections such as those sponsored by Hazelten Foundation, Betty Ford Institute, The Mayo Clinic, various meditation centers as well as other types of educational/ entertainment activities are available by hypertext link on the recorded media.

One of the principal features of the system of the present invention is the quest module by which the system tries to install a form of discipline into persons undergoing recovery and whose profile is often delinquent in many ways, shapes and forms. The quest module attempts to provide the user with readily available tools to achieve disciplinary control over behavior which is out of control.

The first goal of the quest module is to emphasize to the user that quality of life depends in a large measure on lifestyle. It tries to instill habits and behaviors that if performed adequately and regularly will change one's quality of life. A second objective of the quest module is to impress upon the individual that whatever programmed "behavior" they were subjected to early in their life, can be deprogrammed and/or reprogrammed; that they can modify self-defeating strategies with which they have been encumbered during their life. The quest module is hinged upon a routine comprising a work schedule of activities done in the morning, during the day and at night. This enables the individual to come back into the present moment by following a relatively rigid set of procedures and enables them to break the pattern of hopelessly drifting thinking often characterizing dependents and co-dependents. In addition, the quest module conveys through various workshops specific information assisting the individual in surmounting denial with exercises, knowledge and feeling.

Figure 7:
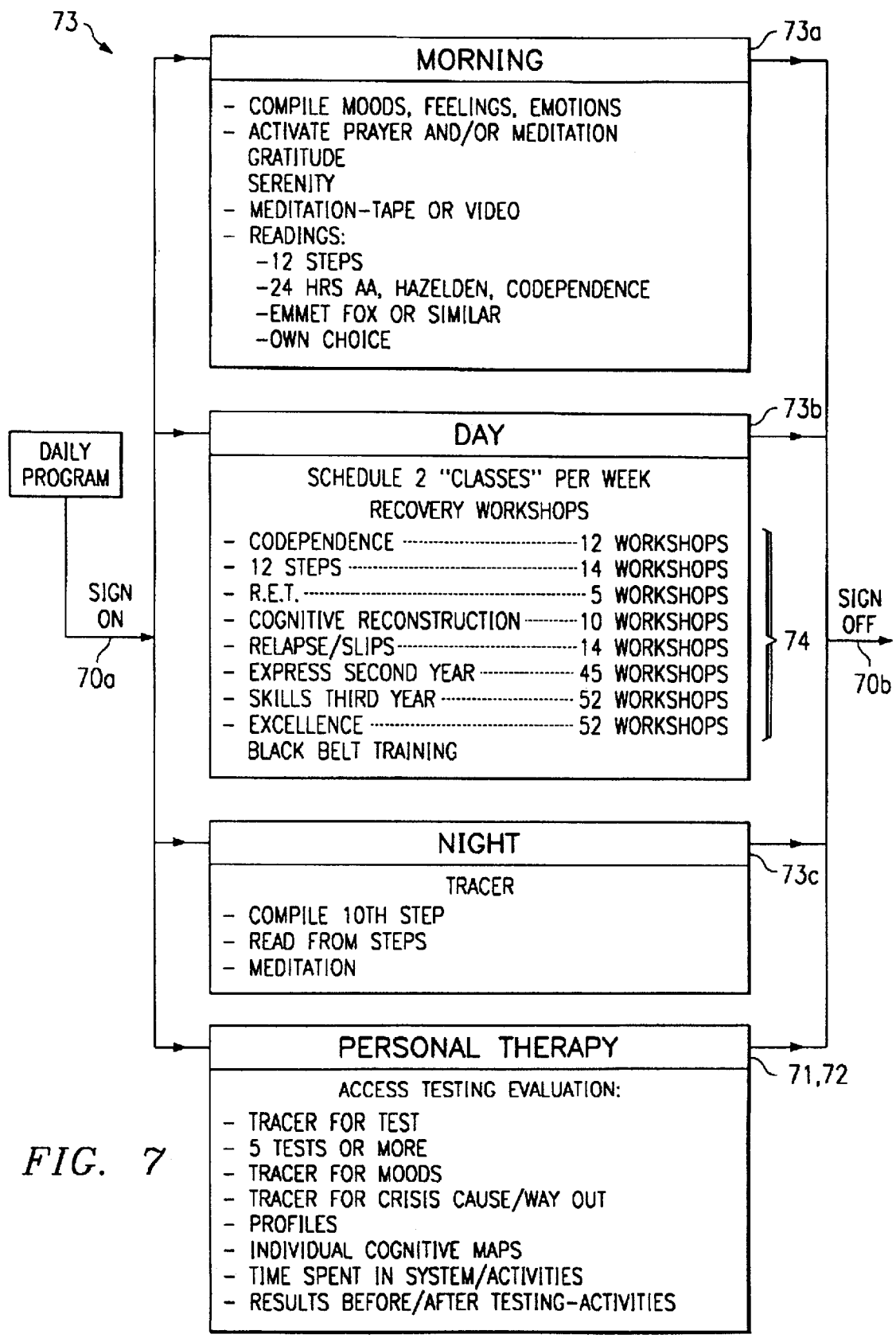
FIG. 7 is a flow chart depicting various aspects of an exemplary quest software module used in the system of the present invention.

Should the user of the system of the present invention choose to access the quest module, as illustrated in the flow chart of FIG. 7, there are also numerous sub-modules available. For example, in the daily program sub-module 73 the user can establish a program for each of the portions of the day: morning, day-time and night. During the morning 73a the user could step through a regular and structured routine including evaluation of the user's present state of mind, and the practice of spiritual related exercises as well as certain readings to provide support and energy for the day. During the day-time period 73b, for example, the user might schedule one of a plurality of workshops 74 with a goal of attending approximately two classes a week. These workshops could be directed to recovery oriented subjects and could be provided in a prerecorded format on the recorded media implementing the system itself, via hypertext links to the Internet or by means of separate video tapes and other programs incorporated into the system. During the night period 73c the user may again be guided through certain evaluation and spirituality practices to close the day. By means of personal therapy, through the self test sub-module 71 and the results sub-module 72, the individual can access a testing and evaluation process for determining both current state of mind as well as longer term progress in the recovery process. As part of the daily program, the system includes a "sign-on" activity 70a as well as a "sign-off" activity 70b. Each of these times are important and useful for the tracing of time spent in the system and as well as the time spent in individual workshops.

The tracer or progress database assembly function of the present invention is extremely useful with respect to providing the user with perspective on progress in the recovery process. This perspective in turn supports and encourages the user that full recovery is not only possible but in process. The tracer function includes a number of different functions as mentioned above. It traces the time of entry and exit to the system as well as time spent in the system and in what modules of the system. This information as well as other data gathered during the tracer function is all stored in memory within the system, for example, in the hard disk 33 of the computer 26. Time spent in various areas helps to monitor the efforts being put into the system by the user. The tracer also keeps track of all test scores administered to the user in both the crisis and quest modules as well as keeps track of accumulated points that are generated as incentive elements via usage of the program itself. Similarly, the tracer keeps track of prizes which may be offered to and awarded to the individual as a result of the accumulation of points through usage. The tracer also keeps track of purchases that the user may make of books, video tapes, and educational programming through the browse and quest modules as well as disbursements for "1-900" phone calls made to therapists and other possible expenses arising as a result of the use of the system.

The tracer, database assembly function additionally keeps a record of all test results and of assessments performed by the system and works as part of the stored database comprising the baseline of the user and similarly stores all of the data collected as a ciphered or encrypted format within memory of the system, for example, hard disk 33 of computer 26. Moreover, the tracer element is an important component of the system and serves to keep track evolution, use, effort, results produced by the user in the course of using the system.

As discussed above, the system of the present invention incorporates a number of different operative principles and tools to produce results. The operative principles and their relationship to tools in effect are illustratively shown in the chart of FIG. 9 and which provide a framework that one of ordinary skill in the art of treating addiction, will understand as a basis for a treatment plan. Basic among these are a series of operative principles that make things happen. These principles include:

(1) Pain—this includes anxiety, depression, sadness and fears. In general, pain is the principal motivator to encourage one to embark on a recovery process.

(2) H.O.W.—these parameters are honesty, openness and willingness. Each of which are required attitudes in order to achieve progress in the recovery process.

(3) Discipline—As with all human endeavors, you get out of anything what you put into it. In the recovery process there is a threshold of discipline which is necessary in order to achieve results. The tools used in implementing this basic principle include tracers i.e. feedback, prizes, as well as daily use in order to achieve the effects of self esteem and results from the efforts.

(4) G.P.S.—This refers to the principle of general purpose spirituality which can either of the faithful or faithless type. Often, such spirituality is forgotten and/or unexplored for most dependents and co-dependents but the system of the present invention establishes a strong connection and support in this realm to provide contents for rational thinking, emotive acceptance and the finding of inner direction. The tools may be the AA twelve step process which provides a sense of direction of past/present/future.

(5) Knowledge—Knowledge and understanding are the mechanisms that govern the behavior of human beings. It is essentially how we became programmed to be the way they are and the way through which we are deprogrammed and/or reprogrammed. In the present invention, knowledge is one of the primary tools in that it is the antithesis of one undergoing recovery's biggest enemy: denial. Knowledge comes through the tools of tests and evaluations, books, workshops and other means and promotes understanding, feasibility and demonstration.

(6) Feelings—Feelings are one of the key players in this program. Feelings are most powerful when they are hidden and unknown but once identified they can be neutralized. The basic tool to deal with feelings is that of introspection which produce the effect of challenging negative feelings and replacing them with ones more productive and healthy.

(7) System—The system of the present invention provides a progression of paced activities that are complimentary to one another. The user knows the sequence, the modules, the tools, the activities and the skills involved. A time is suggested and users can pace themselves. The tool is the program construction itself and the timely pacing of activities which produces maximum results.

(8) Multi-Media Interconnection—One of the major shared universal characteristics of dependents and co-dependents is their high propensity to isolate themselves whenever things go wrong, whether slightly wrong or very wrong. A major advantage of the system of the present invention is that it is based on a computing platform, such as a PC, through which anyone can access all tools from home, hotel room or office all the time, 24 hours a day. This includes the consultation of a therapist 24 hours a day over the phone. Such a system provides a direct antidote to isolation which is greatly counterproductive in the recovery process. The system of the present invention removes the user from a perceived state of isolation while providing the user with the above discussed functionalities in a confidential and private environment.

(9) Individual-tailored-made support—Via sponsorship and therapy the general character of dependency and co-dependency take on a focus of the specific reality of the individual. Specific problems in relation to character defects and deficiencies are worked on, resolved, and replaced by positive behavior. The user works with specifics rather than generalizations and the accurate use of profile and baseline definitions created by the individual as well as the sponsor and therapist provide individually tailored support.

(10) Therapy—Addiction, dependency and co-dependency are caused by a major accident or a crash. The therapies involved in the present system all focus on specific adjustments which have short term and long term results which cannot be produced alone. These adjustments are all discussable, measurable, programmable, complementary to one another and produce both pleasure and relief to the user.

(11) Group support—Some people are able to work out their way without group support. However, it has been found that it is must easier, quicker and more satisfying as well as more gratifying for an individual to tackle the issues with group support whether by interchanges over the Internet or by attending one of the many meetings regularly held by various support fraternities in the United States. Groups break up the habitual isolation of dependents and co-dependents to become a nurturing family that encourages the recovery process and stimulates changed behavior.

(12) H.O.W.—Honesty, openness and willingness are encouraged by reaffirming one's vows to recover one day at a time.

Figure 10:
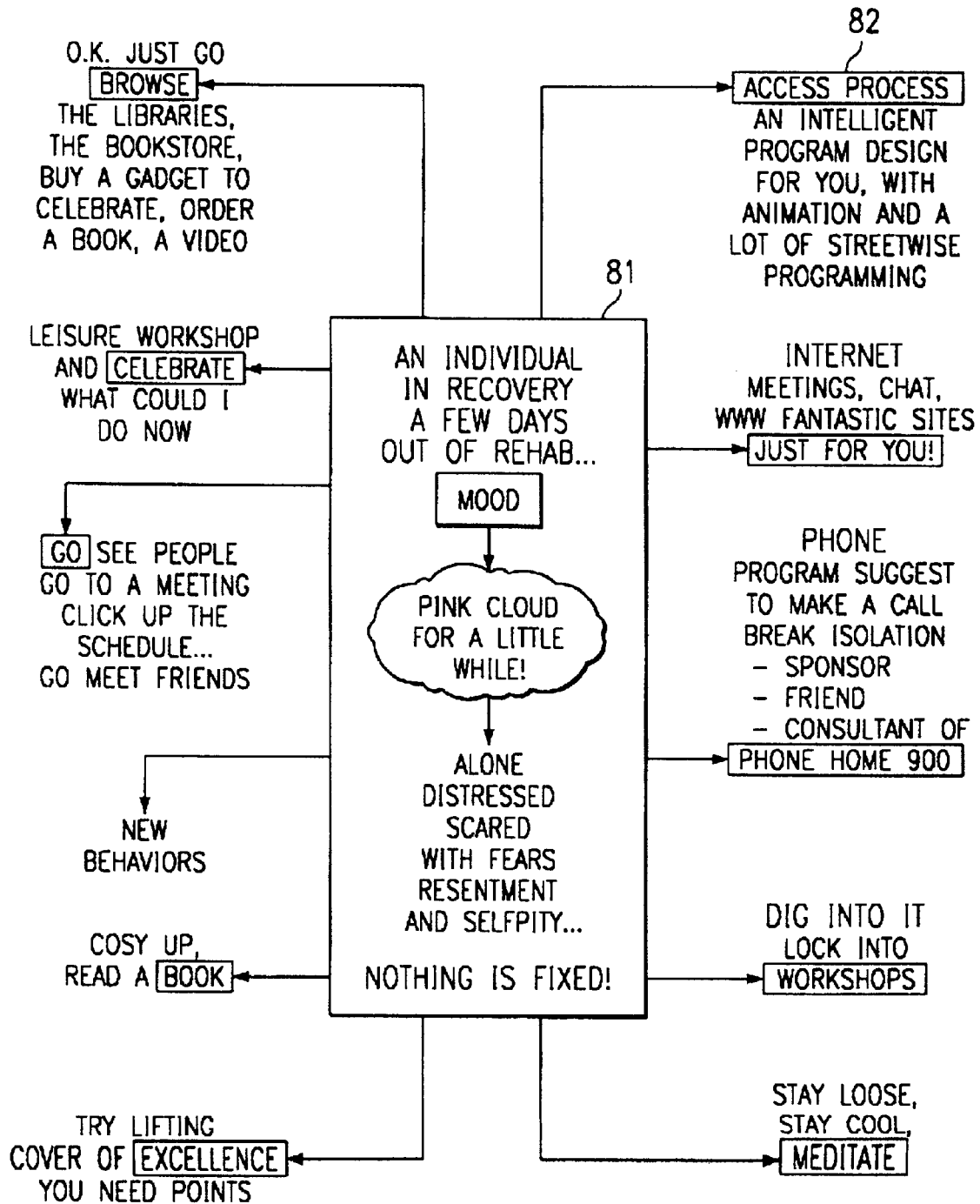
FIG. 10 is a pictorial diagram illustrating additional aspects of the system of the present invention.

Finally, referring to FIG. 10, there is shown a pictorial illustration of part of the process associated with the present invention. As pointed out at 81, an individual who has gone through recent rehabilitation to withdraw to substance may be quite high and encouraged for a short period of time. However, sooner or later the person is faced with aloneness, fears and other emotions which cause that individual to regress or abandon hope for the full recovery process. The system of the present invention includes an interactive way in which an individual achieves support and education on a regular and systematic basis leading to full recovery in an optimal period of time.

Although preferred embodiment of the method and system of the present invention has been illustrated in the accompanying drawings and described in the foregoing detailed description, it is to be understood that the invention is not limited to the embodiments disclosed, but it capable of numerous rearrangements, modifications and substitutions without departing from the spirit of the invention as set forth and defined in the following claims.

What is claimed is:

1. An interactive multi-media system comprising:
a computer system wherein said computer system comprises a central processing unit, a monitor, and a user input means for accepting input from a user and wherein said central processing unit, said monitor and said user input means are interconnected; and a means to read a recorded medium, wherein said recorded medium has data recorded thereon and adapted for interactive engagement with the user of said computer system wherein information on said recorded medium provides recorded data controls such that said recorded medium containing instructions to implement:
 a crisis module for interactively testing and evaluating a user's mental condition and recommending specific procedures to come out of adverse mental conditions depending upon the results of said test;
 a browse module containing resource materials for the user of said computer system related to education in the realm of the recovery process; and
 a quest module containing means for structuring a specific program for the user to follow to further the user's progress in the recovery process; and
 a means to employ either prestored or requested patient information including patient history; and
 means to select and provide from a plurality of possible activities a structured course of activities for the user so as to provide support and guidance to the user, wherein said user is undergoing treatment for the recovery from a substance or emotional dependency and wherein the selection of activities to follow in response said interactive testing and said patient information and history is by use of an inference engine.

2. A multi-media computer system as set forth in claim 1 wherein said crisis module implemented by said recorded medium further includes:

means for enabling said user to select one of a plurality of standardized distress indicating tests;

means for enabling the user to interactively take the selected test on the computer system and evaluating the test to determine a distress level being experienced by the user at that moment and to produce a result indicative of said distress level; and means responsive to the results of said distress indicating test for recommending a proposed action for moderating the distress being experienced by the user.

3. A multi-media computer system as set forth in claim 2 wherein said crisis module implemented by said recorded medium also includes:

means for comparing the results of the one of the plurality of standardized distress indicating test taken by the user with a database of information about the user to facilitate the recommendation of a proposed action for moderating such distress.

4. A method of providing interactive support and training to an individual said method comprising:

providing said individual with a selectable choice from plurality of interactive modules each module comprising information stored on a prerecorded medium in said computer, at least one of said choices includes a computer controlled routine for interactively and wherein said selection is based upon an output from an inference engine, testing said individual to evaluate the level of distress the individual is experiencing at the present moment;

evaluating the result of said test to produce an output; and providing to the individual wherein said individual is undergoing treatment for the recovery from substance/emotional dependency a strategy of action, support and training to alleviate the distress based upon said test output.

5. A method of providing interactive support and training with said individual as set forth in claim 4 wherein at least one of said choices also include:

providing the individual with a selection of a plurality of information banks from which the individual may select data conveying educational information helpful to the individual in the recovery process.

6. A method of providing interactive support and training as set forth in claim 4 wherein at least one of said choices also includes:

accessing a module within said computer system which provides a structured daily routine for the individual undergoing the recovery process.

7. A data carrying medium having data recorded thereon for controlling an interactive computer system, said data including a plurality of software modules, said modules including:

a module for taking and storing user patient histories from an individual undergoing treatment for substance/emotional dependency;

a crisis module containing a plurality of user selectable standardized tests each of which are capable of indicating the distress level of an individual taking the test;

means for interactively receiving test response information from a user and based upon those responses and upon said taken and stored user patient history, evaluating the distress level of the individual completing the test by way of an inference engine; and means responsive to the distress level indicated by the results from the selected test for recommending to the user a specific action to be taken in order to moderate the level of distress indicated by the results.

8. A data carrying medium as set forth in claim 7 wherein said modules include:

means within said interactive test response receiving means for considering said baseline database related to the user in evaluating the distress level of said individual.

9. A data carrying medium as set forth in claim 7 wherein said data gathering module include:

at least one test for evaluating the psychological profile of said individual user.

10. A data carrying medium as set forth in claim 7 which also includes a browse software module comprising the following sub-modules:

means for storing a library of documenatary information related to the recovery process; and means for enabling the user to access a data communcation network connected to various literary resources containing documentary information related to the recovery process.

* * * * *